United States Patent [19]

Allen

[11] Patent Number: 5,779,659
[45] Date of Patent: Jul. 14, 1998

[54] ELASTIC BANDAGE WITH TENSION INDICATOR

[75] Inventor: Kenneth Alfred Allen, Hucknall, England

[73] Assignee: ConvaTec Limited, England

[21] Appl. No.: 791,538

[22] Filed: Mar. 18, 1997

Related U.S. Application Data

[63] Continuation of Ser. No. 446,724, filed as PCT/GB93/02469 Nov. 30, 1993, abandoned.

[30] Foreign Application Priority Data

Dec. 1, 1992 [GB] United Kingdom .................. 9225146

[51] Int. Cl.$^6$ ........................................ A61F 5/00
[52] U.S. Cl. ................................... 602/75; 602/76
[58] Field of Search ........................ 602/19, 53, 75, 602/76, 77, 78

[56] References Cited

U.S. PATENT DOCUMENTS

| | | | |
|---|---|---|---|
| 3,613,679 | 10/1971 | Bijou | 602/75 |
| 4,286,603 | 9/1981 | Marshall | 600/595 |
| 4,421,124 | 12/1983 | Marshall | 600/595 |
| 4,437,408 | 3/1984 | Arkans | 101/426 |
| 5,195,950 | 3/1993 | Delannoy | 602/72 |
| 5,503,620 | 4/1996 | Danzger | 602/19 |

FOREIGN PATENT DOCUMENTS

| | | |
|---|---|---|
| 475811 | 3/1992 | European Pat. Off. . |
| 8102320 | 8/1982 | France . |
| 3640979 | 8/1987 | Germany . |

Primary Examiner—Richard J. Apley
Assistant Examiner—Kim M. Lee
Attorney, Agent, or Firm—Young & Basile, P.C.

[57] ABSTRACT

An elasticated bandage has knitted therein a geometrical pattern comprising two components which adopt recognizable configurations when the bandage is extended to corresponding predetermined degrees. Preferably, the two components are alternating large and small rectangles arranged with colinear short edges. When the bandage is stretched, the short sides of the rectangles become lengthened. In each case, a point is reached at which the short and long sides of the rectangle becomes square, and this indicates that a pre-determined tension has been reached.

21 Claims, 1 Drawing Sheet

ELASTIC BANDAGE WITH TENSION INDICATOR

This application is a continuation of application Ser. No. 08/446,724, filed on May 30, 1995, now abandoned.

This claims the benefit of prior filed copending international application number PCT/GB93/02469 filed Nov. 30, 1993.

BACKGROUND OF THE INVENTION

This invention relates to bandages, in particular to elasticated bandages of the type which have to be applied in such a way as to exert a pre-determined sub-bandage pressure.

Bandages applied to certain wounds, e.g. leg ulcers, have to be applied in such a way as to exert a pre-determined sub-bandage pressure. The optimum pressure will be determined by medical or nursing staff according to the nature and severity of the wound. The bandages which are applied are elasticated and pressure exerted is a function of the degree of extension of the bandage and the circumference of the limb to which it is applied. For one commercially available bandage, for example, the following table is published:

TABLE I

| Extension | Pressure exerted/mm Hg Limb circumference/cm | | |
|---|---|---|---|
| | 18–26 | 27–35 | 36–50 |
| 50% | 36–25 | 24–18 | |
| 75% | 50–37 | 37–28 | 28–19 |

In use, a nurse faced with the task of applying such a bandage must first measure or estimate the circumference of the patient's limb and then apply the bandage with the correct degree of extension to achieve the prescribed pressure. This is a difficult operation to perform with any degree of accuracy, with the result that incorrect pressure is often achieved. This may cause sub-optimal healing, or discomfort for the patient.

In an attempt to overcome this problem, it has been proposed (see Journal of Wound Care, Sept/Oct 1992, page 23 onwards) to print on a bandage a visual aid in the form of similar rectangles which, when the bandage is stretched to a predetermined extension, take the shape of squares. A disadvantage of this arrangement is that the nurse must still estimate the circumference of the limb and then try to choose the extension which will give rise to the required sub-bandage pressure for that limb. Since the extension at which the rectangles become square will only be appropriate for one limb size, the visual aid is of limited utility.

A further disadvantage of this arrangement is that the printing of the pattern on the bandage results in a non-uniform, non-smooth surface having "high spots" which may give rise to irritation of the wound or other harmful effects. There is also a risk that the printing ink or marker substance may give rise to allergic reactions with some patients, which cannot be predicted. The problem is particularly acute, since the printing ink is generally inflexible and may therefore crack when the bandage is extended and particles of ink may become dislodged, thereby contaminating the wound.

SUMMARY OF THE INVENTION

There has now been devised an improved form of elasticated bandage which overcomes or substantially mitigates the above-mentioned disadvantages.

According to the invention, there is provided an elasticated bandage bearing a geometrical pattern comprising two components which adopt recognizable configurations when the bandage is extended to corresponding pre-determined degrees.

The bandage according to the invention is advantageous in that it provides a direct visual indication of the attainment of a particular extension (and hence of a certain tension in the bandage, giving rise to a certain sub-bandage pressure), without the need for a quantitative estimation of the limb circumference.

It is particularly preferred that the different degrees of extension at which the two components attain their recognizable configurations should correspond to the bandage tensions most commonly required in practice. We have found that bandage tensions of 1N and 1.5N are suitable for a wide range of limb sizes. In a preferred embodiment, therefore, the two components of the pattern adapt their recognizable configuration when the bandage tension is 1N and 1.5N respectively. The lower tension is appropriate for smaller limbs, and the higher tension for larger limbs. A nurse applying the bandage need only make a qualitative assessment of the limb size as being either "large" or "small" and extend the bandage until the respective recognizable configuration is attained.

According to a second aspect of the invention, therefore, there is provided an elasticated bandage bearing a geometrical pattern which adopts a recognizable configuration when the bandage is extended to a pre-determined tension.

Preferably, the bandage when applied to a limb gives rise to a pressure at the ankle of at least 40 mm Hg.

The geometrical pattern born by the bandage most preferably comprises rectangles, the short sides of which lie parallel to the longitudinal axis of the bandage, and the longer sides transverse to the bandage. Extension of the bandage along its long axis will elongate the short sides of the rectangle. A point is reached at which the short sides are the same length as the long sides. In this condition, the rectangle has become a square which is recognizable as such and thus indicates that the required extension has been reached.

Experience has shown that the point at which the rectangle becomes a square is readily detectable by the user, and achieving substantially the requisite degree of tension is reproducible. If the requisite tension is attained at 50% extension, the ratio between the lengths of the long and short sides of the rectangle should be 3:2 in the unstretched condition. If the requisite tension is attained at 75% extension, the ratio should be 7:4.

The rectangles (or other components of the pattern) may be discrete or may be linked. The components are preferably provided on the same side of the bandage, though they may alternatively be on opposite sides of the bandage.

It is, however, particularly preferred that the two components be alternating large and small rectangles. Most preferably, the large and small rectangles are arranged with colinear short edges. Together, the colinear short edges preferably form a continuous line running the length of the bandage. Advantageously, the said line is located half-way between the bandage longitudinal edges, and performs the function of the central application guide line conventionally present on such bandages. This application guide line is important since the sub-bandage pressure depends on the degree of overlap with which the bandage is applied, and 50% overlap is conventionally used.

Of course, apart from rectangles, any other geometrical pattern may be used, e.g. lozenges, patterns of dots, etc. However, for the reasons given above, rectangles are preferred.

Although two components in the pattern are generally sufficient for practical purposes, e.g. to indicate the two extremes of an operating range or two pre-determined tension, it is of course possible for further components to be provided. One example would be rectangles of three different proportions, indicating three different pre-determined tensions.

The geometrical pattern may be printed on the bandage. However, it is preferred that the pattern should be part of the structure of the fabric i.e. it should be knitted or woven into the fabric. This prevents any real or perceived differences in the thickness or feel of the bandage, and eliminates the problem of physiological reactions to the printing ink used.

According to a further aspect of the invention, there is provided a knitted elasticated bandage having knitted therein a geometrical pattern formed with yarn of a color contrasting to that of the reminder of the bandage, the pattern being such that it adopts a recognizable configuration when the bandage is longitudinally extended by a pre-determined amount.

In color, the bandage will generally be white or flesh-colored. Most preferable, the geometrical pattern is yellow or orange since this color is easily visible on such a light background and is also easily seen by persons who suffer from color-blindness.

Apart from the provisions of the geometrical pattern, the bandage of the present invention may be generally conventional in construction, and may be manufactured using techniques, e.g. machine knitting, which are conventionally used for the manufacture of elasticated bandages. In line with conventional machine-knitting practice, the pattern may be formed using pattern bars which are driven to reciprocate by suitable camming arrangements.

BRIEF DESCRIPTION OF THE DRAWINGS

The invention will now be described in greater detail, by way of illustration only, with reference to the accompanying drawings in which.

DETAILED DESCRIPTION OF THE PREFERRED EMBODIMENT

Figure 1:
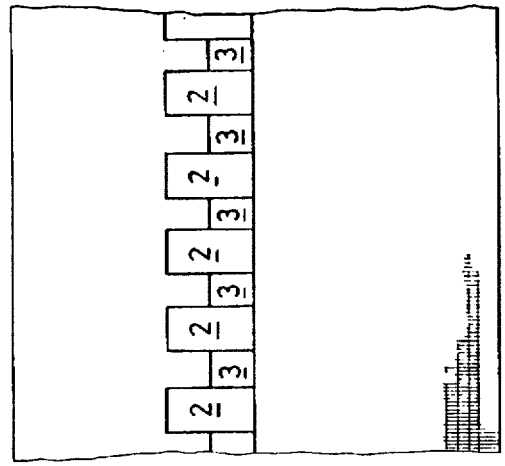
FIG. 1 is a plan view of part of an elasticated bandage according to the presently preferred embodiment of the invention in the unstretched condition.

Referring first to FIG. 1, an elasticated bandage (generally designated 1) comprises a band approximately 10 cm wide of elasticated knitted fabric. The preferred bandage is made from a Lycra elastomer, a cotton-viscose blend yarn, and nylon.

Knitted into the structure of the bandage 1, longitudinally of the bandage, is a geometrical pattern comprising a line of alternating small and large rectangles (2, 3 respectively). The longer sides of both small and large rectangles 2, 3 are arranged transverse to the longitudinal axis of the bandage 1, the shorter sides being parallel to the axis. The pattern of rectangles 2, 3 is knotted in yellow yarn, the remainder of the fabric band being "off-white", i.e. flesh-colored.

Figure 3:
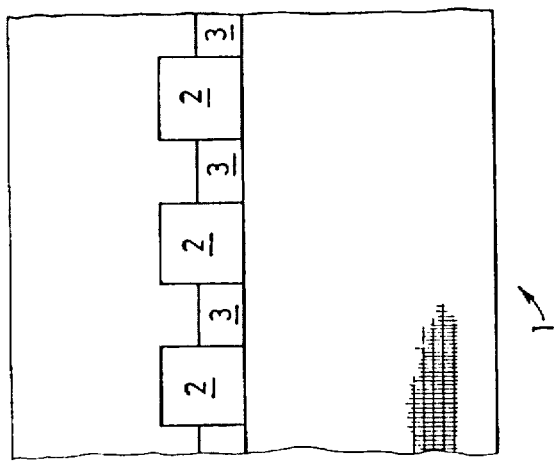
FIG. 3 shows the bandage of FIG. 1 extended to a second, greater pre-determined tension.
Figure 2:
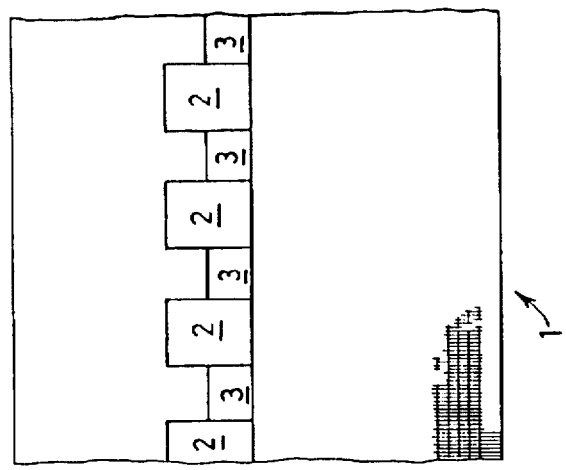
FIG. 2 shows the bandage of FIG. 1 extended to a first pre-determined tension.

The smaller rectangles 2 measure 11 mm×7.5 mm; the larger rectangles 3 21 mm×12 mm. When the bandage 1 is stretched, the shorter sides of the rectangles 2, 3 become longer. When the bandage is stretched to the first pre-determined tension (as shown in FIG. 2), which in this case occurs at 50% extension, the longer and shorter sides of the smaller rectangles 2 become approximately equal in length and the smaller rectangles 2 become squares. Similarly, when the bandage is stretched a second, greater pre-determined tension, in this case occurring at 75% extension, the larger rectangles 3 become square, as shown in FIG. 3.

The first pre-determined tension is approximately 1N. At this tension, the sub-bandage pressure for a patient with a relatively small limb circumference is about 45 mm Hg. Hence, for such a patient, to apply a compressive force of 45 mm Hg, the bandage 1 is stretched until the smaller rectangles 2 become square, i.e. to a tension of 1N. For a higher compressive force, say of 68 mm Hg, the bandage is stretched until the larger rectangles 3 become square, i.e. beyond the point at which the smaller rectangle rectangles 2 become square, but before the larger rectangles 3 become square. For a patient with a relatively large limb circumference, a sub-bandage pressure of about 45 mm Hg is achieved at the second pre-determined tension, i.e. at the extension at which the larger rectangles 3 become square.

In the known bandage in which a pattern is printed on the bandage material, the recognition of the rectangles changing to squares is provided to assure the bandage that the extension achieved is a desired amount, e.g. 50%. In contrast, in the present invention as particularly described the recognition of the rectangles taking up square configurations assures the bandage that the right amount of tension and thus a suitable sub-bandage pressure, e.g. 40 mm Hg or above has been applied. Only a qualitative estimation of the limb circumference is required.

I claim:

1. An elastic bandage having first and second longitudinal edges and bearing a geometrical pattern, comprising:
   two components which adopt recognizable configurations when the bandage is extended to corresponding pre-determined degrees, said two components being alternating large and small rectangles each having first and second short sides which lie parallel to the longitudinal axis of the bandage and first and second longer sides which lie transverse to the bandage, the first short sides of the large and small rectangles being collinear and together forming a centrally disposed application guide line located half-way between the first and second longitudinal edges.

2. A bandage as claimed in claim 1, wherein the degrees of extension at which said two components attain their recognizable configurations correspond to tensions generated in the bandage by exerting force across the width of the bandage of approximately 1N and 1.5N respectively.

3. A bandage as claimed in claim 2, wherein the bandage when applied to a limb gives rise to a pressure at the ankle of at least 40 mm Hg.

4. A bandage as claimed in claim 3, wherein the rectangles are contiguously linked such that the application guide line is a continuous line located midway between the bandage longitudinal edges.

5. A bandage as claimed in claim 4, wherein the bandage is white or flesh-colored, and the geometrical pattern is yellow or orange.

6. A bandage as claimed in claim 5, wherein the pattern is knitted into the structure of the fabric.

7. A bandage as claimed in claim 6, wherein the geometrical pattern is formed with a yarn of a color contrasting to that of the remainder of the bandage.

8. A bandage as claimed in claim 2, wherein adjacent rectangles share at least a portion of a longer side.

9. A bandage as claimed in claim 2, wherein the pattern is knitted into the structure of the fabric.

10. A bandage as claimed in claim 9, wherein the geometrical pattern is formed with a yarn of a color contrasting to that of the remainder of the bandage.

11. A bandage as claimed in claim 2, wherein the geometrical pattern adopts a recognisable configuration when the bandage is extended to a pre-determined tension.

12. A bandage as claimed in claim 1, wherein the bandage when applied to a limb gives rise to a pressure at the ankle of at least 40 mm Hg.

13. A bandage as claimed in claim 1, wherein the rectangles are contiguously and continuously linked such that the application guide line is a continuous and unbroken line located midway between the first and second longitudinal edges.

14. A bandage as claimed in claim 1, wherein the bandage is white or flesh-colored, and the geometrical pattern is yellow or orange.

15. A bandage as claimed in claim 1, wherein the pattern is knitted into the structure of the fabric.

16. A bandage as claimed in claim 15, wherein the geometrical pattern is formed with a yarn of a color contrasting to that of the remainder of the bandage.

17. A bandage as claimed in claim 1, wherein a first longer side of one of the rectangles forms at least a portion of the second longer side of an adjacent rectangle.

18. An elastic bandage bearing a geometrical pattern, comprising:

components which adopt a recognizable configuration when the bandage is extended to a predetermined degree, said components being rectangles having short sides which lie parallel to the longitudinal axis of the bandage and longer sides which lie transverse to the bandage, the short sides of the rectangles being co-linear and together forming an application guide line located between the bandage longitudinal edges.

19. The elastic bandage of claim 18, wherein the guide line is continuous and unbroken.

20. An elastic bandage bearing a geometrical pattern, comprising:

components which adopt a recognizable configuration when the bandage is extended to a predetermined degree, said components being rectangles having short sides which lie parallel to the longitudinal axis of the bandage and longer sides which lie transverse to the bandage, the short sides of the rectangles being co-linear and together forming a centrally disposed application guide line located halfway between the bandage longitudinal edges.

21. The elastic bandage of claim 20 wherein the guide line is a solid continuous line.

* * * * *